United States Patent [19]

Vidal et al.

[11] 4,257,972
[45] Mar. 24, 1981

[54] CATALYST FOR PRODUCING POLYHYDRIC ALCOHOLS AND DERIVATIVES

[75] Inventors: José L. Vidal, Charleston; Wellington E. Walker, Sissonville, both of W. Va.

[73] Assignee: Union Carbide Corporation, New York, N.Y.

[21] Appl. No.: 62,357

[22] Filed: Jul. 31, 1979

Related U.S. Application Data

[60] Division of Ser. No. 958,383, Nov. 7, 1978, Pat. No. 4,180,517, which is a continuation-in-part of Ser. No. 880,080, Feb. 22, 1978, abandoned.

[51] Int. Cl.$^3$ .............................................. C07F 15/00
[52] U.S. Cl. .......................... 260/429 R; 252/431 N; 423/306
[58] Field of Search ..................... 260/429 R; 423/306

[56] References Cited

U.S. PATENT DOCUMENTS

| 3,948,965 | 4/1976 | Cawse | 252/431 N X |
| 4,115,433 | 9/1978 | Cosby et al. | 260/429 R X |
| 4,133,776 | 1/1979 | Pruett et al. | 252/431 N |

*Primary Examiner*—Helen M. S. Sneed
*Attorney, Agent, or Firm*—Franklyn Schoenberg

[57] ABSTRACT

A novel catalyst and process for the manufacture of polyhydric alcohol(s) from synthesis gas. This novel catalyst is a rhodium carbonyl phosphido cluster compound. In particular, the anion cluster of the rhodium carbonyl phosphido compound is of the following empirical formula:

$$[Rh_9P(CO)_{21}]^{-2}$$

3 Claims, No Drawings

CATALYST FOR PRODUCING POLYHYDRIC ALCOHOLS AND DERIVATIVES

This application is a division of application Ser. No. 958,383, filed Nov. 7, 1978, now U.S. Pat. No. 4,180,517 which in turn is a continuation-in-part of application Ser. No. 880,080, filed Feb. 22, 1978, now abandoned.

This invention relates to the production of polyhydric alcohols, in particular alkane polyols, as well as a variety of other chemicals, in particular methanol. The invention is also concerned with a novel catalyst for producing such products from synthesis gas, i.e., a mixture of carbon monoxide and hydrogen.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making alkane diols, triols, tetraols, etc., containing 2, 3, 4 or more carbon atoms. A key product of the process of this invention is ethylene glycol. By-products of this invention are the lesser valuable, but nonetheless valuable, monohydric alkanols such as methanol, ethanol and propanol. The products of the process of this invention contain carbon, hydrogen and oxygen.

There are described in U.S. Pat. No. 3,833,634 issued Sept. 3, 1974, and U.S. Pat. No. 3,957,857, issued May 18, 1976, processes for reacting hydrogen and oxides of carbon in the presence of rhodium carbonyl complex catalysts. U.S. Pat. No. 3,957,857 is concerned with a rhodium carbonyl complex which is a rhodium carbonyl cluster exhibiting a particular infrared spectrum. The conditions employed in those processes involve reacting a mixture of an oxide of carbon and hydrogen with a catalytic amount of rhodium in complex combination with carbon monoxide, at a temperature of between about 100° C. to about 375° C. and a pressure of between about 500 p.s.i.a. to about 50,000 p.s.i.a.

In addition to the aforementioned U.S. Patents, the following U.s. Patents and U.S. Patent applications amplify the development of the processes for making alkane polyols from mixtures of hydrogen and oxides of carbon:

U.S. Pat. No. 3,878,292, Patented Apr. 15, 1975
U.S. Pat. No. 3,878,290, Patented Apr. 15, 1975
U.S. Pat. No. 3,878,214, Patented Apr. 15, 1975
U.S. Pat. No. 3,886,364, Patented May 27, 1975
U.S. Pat. No. 3,940,432, Patented Feb. 24, 1976
U.S. Pat. No. 3,929,969, Patented Dec. 30, 1975
U.S. Pat. No. 3,952,039, Patented Apr. 20, 1976
U.S. Pat. No. 3,948,965, Patented Apr. 6, 1976
U.S. Pat. No. 3,944,588, Patented Mar. 16, 1976
U.S. Pat. No. 3,957,857, Patented May 18, 1976
U.S. Pat No. 3,974,259, Patented Aug. 10, 1976
U.S. Pat. No. 3,989,799, Patented Nov. 2, 1976
U.S. Pat. No. 4,013,700, Patented Mar. 22, 1977
U.S. Pat. No. 3,968,136, Patented July 6, 1976
U.S. Pat. No. 4,001,289, Patented Jan. 4, 1977
U.S. Ser. No. 511,740, Filed Oct. 3, 1974
U.S. Ser. No. 618,021, Filed Sept. 30, 1975
U.S. Ser. No. 782,986, Filed Mar. 30, 1977 (now U.S. Pat. No. 4,111,975, patented Sept. 5, 1978).
U.S. Ser. No. 615,093, Filed Sept. 19, 1975

It has been found that rhodium carbonyl phosphido cluster compounds wherein the anion is of the following empirical formula:

$$[Rh_9P(CO)_{21}]^{-2}$$

are effective to provide the catalysts for the production of polyhydric alcohol(s) from synthesis gas. Moreover, the rhodium carbonyl phosphido clusters of this invention are almost unique in their stability when employed in the production of alkane polyols from the homogeneous catalytic reaction of synthesis gas. They are not as dependent upon solvent selection in carrying out this process to avoid catalyst losses. Thus rhodium cluster stability in the reaction can be achieved with a greater variety of solvents, even in the recovery of the alkane polyol in the recovery phase.

The novel rhodium carbonyl phosphido cluster compound of the present invention is a combination of a cluster anion associated with a cation.

P. Chini, in a review article entitled "The Closed Metal Carbonyl Clusters" published in Review (1968), Inorganic Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster."

The rhodium carbonyl phosphido cluster anion of this invention is in the form of a cubic anti-prism containing phosphorus inside the cluster's cage. Every one of the rhodium atoms has a terminal bonded carbonyl while the remaining twelve bridging carbonyls are believed to be located in the following way: a set of four carbonyls placed between the apical rhodium and the four rhodium atoms in the upper square, another set of four carbonyls placed along the edges of the prism, the remaining set of four carbonyls are placed along the edges of the basal square, and one of the square faces of the anti-prism is capped by the remaining rhodium atom.

The rhodium carbonyl phosphido cluster anion is characterized by the following empirical formula:

$$[Rh_9P(CO)_{21}]^{-2}$$

The cluster exhibits an infrared spectral pattern in acetone which is characterized by two significant infrared bands at about 2010 cm$^{-1}$ and about 1815 cm$^{-1}$, each plus or minus 15 cm$^{-1}$.

The cations which may be used with the rhodium carbonyl phosphido anion include alkali metal and alkaline earth metal cations, organic cations such as $[(C_6H_5)_3P]_2N^{30}$, $R_4N^+$, $R_{4-n}R_nN^+$, wherein R is alkyl or aryl and n is a positive integer from 0 to 4, and other positively charged species that would form a salt with $[Rh_9P(CO)_{21}]^{-2}$. The preferred cations include Cs$^+$, and $[C_6H_5CH_2N(C_2H_5)_3]+$. The cations are generally added to the reaction in the form of salts.

Illustrative salts which are useful in the practice of this invention are the ammonium salts and the salts of the metals of Group I and Group II of the Periodic Table (Handbook of Chemistry and Physics—50th Edition), for instance the halide, hydroxide, alkoxide, phenoxide and carboxylate salts such as sodium fluoride, cesium fluoride, cesium pyridinolate, cesium formate, cesium acetate, cesium benzoate, cesium p-methylsulfonyl-benzoate (CH₃SO₂C₆H₄COO)Cs, rubidium acetate, magnesium acetate, strontium acetate, ammonium formate, ammonium benzoate and the like. Preferred are the cesium and ammonium carboxylate salts, most preferably their formate, benzoate and para-lower alkyl sulfonyl benzoate salts.

Also useful in the practice of the present invention are organic salts of the following formula:

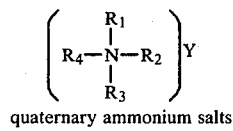

quaternary ammonium salts

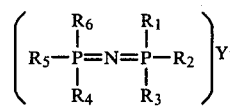

wherein $R_1$ through $R_6$ in formulas (I) and (II) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups, cyclopentyl, cyclohexyl, and bicyclo[2.2.1]heptyl groups, and the like; or an aryl, alkylaryl, or aralkyl group such as phenyl, naphthyl, xylyl, tolyl, t-butylphenyl, benzyl, beta-phenylethyl, 3-phenylpropyl and the like; or a functionally substituted alkyl such as beta-hydroxyethyl, ethoxymethyl, ethoxyethyl, phenoxyethyl, and the like; or a polyalkylene ether group of the formula $-(C_nH_{2n}O)_x OR$ wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas (I) and (II) above may be any anion which does not adversely affect the production of polyhydric alcohols in the practice of the present invention such as hydroxide; a halide, for instance fluoride, chloride, bromide and iodide; a carboxylate group, such as formate, acetete, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pryidinolate or quinolate group; and others. Preferably Y in formulas (I) and (II), above, is a carboxylate, most preferably formate, acetate and benzoate.

A suitable method for preparing the bis(triorganophosphine)iminium salts is disclosed in an article by Appel, R. and Hanas, A. appearing in Z. Anorg. u Allg. Chem., 311, 290, (1961).

Other organic salts useful in the practice of the present invention include the quaternized heterocyclic amine salts such as the pyridinium, piperidinium, morpholinium, quinolinium salts and the like, e.g., N-ethylpyridinium fluoride, N-methylmorpholinium benzoate, N-phenylpiperidinium hydroxide, N,N'-dimethyl-2,2-bipyridinium acetate, and the like.

Under reaction conditions the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The process of this invention which involves the reaction between carbon monoxide and hydrogen in the homogeneous liquid phase mixture, is carried out at a temperature of between about 210° C. to about 320° C., and preferably between about 250° C. to about 300° C. sufficient to produce the alkane polyol. The process is also conducted under superatmospheric pressure. Pressures between about 1,000 pounds per square inch absolute (psia) and about 50,000 psia, and higher, can be employed but with no apparent advantages attendant thereto which offset the unattractive plant investment outlay required for such high pressure equipment. Therefore, the upper pressure limitation is desirably approximately 16,000 psia. Effecting the present process below about 16,000 psia, especially below about 13,000 psia, and preferably at pressures below about 8000 psia, results in cost advantages which are associated with low pressure equipment requirements. In attempting to foresee a commercial operation of this process, pressures between about 4,000 psia and 20,000 psia appear to represent most realistic values. Preferably, pressures in the range of about 4,000 psia to about 20,000 psia are utilized.

In practicing the process of this invention, the reaction (or residence) time utilizing the catalyst system, as aforedescribed, can range from about fractions of a second to as long as 3 to 4 hours or more, depending upon the conditions selected; milder conditions providing longer residence times whereas more aggressive conditions in terms of pressure and temperature reducing the residence time.

The reaction is effected with a normally liquid organic solvents as are described in U.S. Pat. Nos. 3,833,634 and 3,957,857. The description of solvents as contained in those patents is incorporated herein by reference. Also, the crown ethers are suitable herein, particularly those as described in U.S. patent application Ser. No. 832,384 filed Sept. 13, 1977, which application is incorporated herein by reference. The crown ethers described therein contain at least four oxygen hetero-atoms and include [18]-crown-6 and [15]-crown-5.

The preferred solvents for practicing the invention are a number of solvents which have heretofore been described in the production of alkane polyols from synthesis gas.

Particularly desirable solvents are tetraglyme, gamma-butyrolactone and the crown ethers. Other very desirable solvents include mixtures of crown ethers and tetraglyme, mixtures of crown ethers and butyrolactone, and mixtures of tetraglyme and butyrolactone.

The rhodium carbonyl phosphido salt can be prepared by reacting rhodium dicarbonylacetylacetonate and trialkyl or trialryl phosphorous in the presence of alkali metal salts and ether-like solvents such as tetraglyme. The mixture is charged to an autoclave and 500–5000 psig of carbon monoxide and hydrogen are introduced. The system is heated to 100° to 160° C. and allowed to react for about twelve hours. The solution is then placed into a Schlenck received evacuated and flushed with nitrogen. A solvent, such as toluene, is then added. The solvent is decanted after about twelve hours. A tar-like oily residue is extracted with acetone.

The resulting filtrate is vacuum dried and the resulting solid is M[Rh$_9$P(CO)$_{21}$], (wherein M is an alkali metal cation.)

The quantity of cluster compound employed is not narrowly critical and can cary over a wide range. In general, the process of preparing alkane diols and is desirably conducted in the presence of a catalytically effective quantity of the cluster compound which gives a suitable and reasonable reaction rate. Reaction proceeds when employing as little as about $1 \times 10^{-6}$ weight percent, and even lesser amounts, of rhodium (calculated as the metal in the cluster compound) based on the total weight of reaction mixture. The upper concentration limit can be quite high, e.g., about one weight percent rhodium and higher, and the realistic upper limit in practicing the invention appears to be dictated and controlled more by economics in view of the exceedingly high cost of rhodium compounds. No particular advantages at relatively high concentrations of rhodium are manifest. Depending on various factors such as the partial pressures of oxides of carbon and hydrogen, the total operative pressure of the system, the operative temperature, the choice of the normally-liquid diluent, and other considerations, a cluster concentration of from about $1 \times 10^{-5}$ to about 10 weight percent rhodium (contained in the complex catalyst) based on the total weight of reaction mixture, is generally desirable in the practice of the invention.

A number of nitrogen and/or oxygen containing bases may be used in the catalytic process of the present invention. For the purposes of this invention the bases can be considered to promote the activity of the instant rhodium catalyst.

Nitrogen Lewis bases used as promoters generally contain hydrogen and nitrogen atoms. They may also contain carbon and/or oxygen atoms. They may be organic or inorganic compounds. With respect to the organic compounds, the carbon atoms can be part of an acyclic and/or cyclic radical such as aliphatic, cycloaliphatic, aromatic (including fused and bridged) carbon radicals, and the like. Preferably, the organic Lewis bases contain from 2 to 60, most preferably 2 to 40 carbon atoms. The nitrogen atoms can be in the form of imino (—N═), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic),

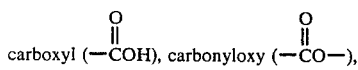
carboxyl (—COH), carbonyloxy (—CO—), oxy (—O—),

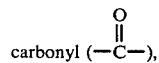
carbonyl (—C—), etc., all of said groups containing Lewis base oxygen atoms. In this respect, it is the "hydroxyl" oxygen in the

—COH group and the "oxy" oxygen in the

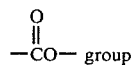
—CO— group that are acting as Lewis base atoms. The organic Lewis bases may also contain other atoms and/or groups as substituents of the aforementioned radicals, such as alkyl, cycloalkyl, aryl, chloro, trialkylsilyl substituents.

Illustrative of organic aza-oxa Lewis bases are, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine, 2,6-dimethoxypyridine, 2-ethoxypyridine, lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(-2-hydroxyethyl)iminodiacetic acid, ethylenediamine-tetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Other Lewis base nitrogen containing compounds include organic and inorganic amines.

Illustrative of such inorganic amines are, e.g., ammonia, hydroxylamine, and hydrazine. Primary, secondary, or tertiary organic amines are promoters. This includes the mono- and polyamines (such as di-, tri-, tetraamines, etc.) and those compounds in which the Lewis base nitrogen forms part of a ring structure as in pyridine, quinoline, pyrimidine, morpholine, hexamethylene tetraamine, and the like. In addition any compound capable of yielding an amino nitrogen under the reaction conditions of the present invention are promoters, as in the case of an amide, such as formamide, cyanamide, and urea, or an oxime. Further illustrative of these Lewis base nitrogen compounds are aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2-ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-toluidine, N,N,N',N'tetramethyl-p-phenylenediamine, N,N,N',N'-tetraethyl-4,4'-biphenyldiamine, and the like; aromatic amines such as aniline, 1-naphthyl, amine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylamino-naphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6,-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2-methyl-N-methylpiperazine; 2,2'-dipyridyl, methyl-substituted 2,2'-dipyridyl; ethyl-substituted 2,2'-dipyridyl; 4-triethylsilyl-2,2' dipyridyl; 1,4-diazabicyclo[2.2.2]octane, methyl substituted 1,4-diazabicyclo [2.2.2]octane, purine and the like.

Also included herein are the use of dimorpholine compounds characterized by the formula:

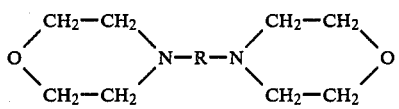

wherein R is divalent alkylene of 1 to about 30 carbon atoms and 1,4-phenylene.

The amine provided to the reaction mixture is present in an amount which is equal to or greater than that amount, determined from the amine's basicity, which achieves the optimum rate of formation of said alkane polyol at said correlated catalyst concentration, temperature and pressure of such reaction mixture.

The concentration of the amine will typically be within about 0.001 to about 10 molar. Obviously this range is definitive of the potential scatter of concentrations predicated on the varities of amine basicity available.

Under reaction conditions the amine is preferably used in amounts from about 0.02 to about 40 equivalents of amine, most preferably from about 0.1 to about 20 equivalent of amine, for every atom of rhodium in the reaction mixture. The number of equivalents of amine is equal to the number of atoms of amine times the number of nitrogen atoms in each molecule.

In practicing the method of the present invention, the synthesis of the desired alkane diols and derivatives thereof, by the reaction of hydrogen with an oxide of carbon is suitably conducted under operative conditions, as heretofore described, which give reasonable reaction rates and/or conversions.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As indicated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as distillation, fractionation, extraction, and the like. A fraction comprising rhodium catalyst, generally contained in byproducts and/or normally liquid organic diluent, can be recycled to the reaction zone, if desired. All or a portion of such fraction can be removed for recovery of the rhodium values or regeneration to the active catalyst and intermittently added to the recycle stream or directly to the reaction zone.

The active form of the rhodium carbonyl phosphido cluster may be prepared by various techniques as heretofore described. They can be preformed and then introduced into the reaction zone or they can be formed in situ. In preparing the rhodium carbonyl phosphido cluster in situ, trialkly or triaryl phosphine is added to a catalytic system based on rhodium dicarbonylacetylacetonate, (Rh/P molar ratios approximately 9 to 12) in an ether-like solvent containing alkali metal salts and/or amines. Thus, a catalytic system is provided without the need for separately isolating the phosphido, $[Rh_9P(CO)_{21}]^{-2}$.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. Nos. 3,957,857, the disclosure of which is incorporated herein by reference.

A particularly desirable infrared cell construction is described in U.S. Pat. No. 3,886,364, issued May 27, 1975, and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably, the oxide of carbon is carbon monoxide.

The following examples are merely illustrative and are not presented as a definition of the limits of the invention.

EXAMPLE 1

Preparative Method and Analytical Results For $Cs_2[Rh_9P(CO)_{21}]$

Rhodium dicarbonylacetylacetonate (12.0 g) was added to 1000 ml. of tetraglyme containing 2.4 g of $CsC_6H_5CO_2$. Triphenyl phosphine (2.10 g) was then added to the tetraglyme solution, resulting in the solution turning a green color which changed to yellow and then to the final brown color of the solution. The solution was then charged to a high pressure autoclave and 4000–5000 psig of carbon monoxide and hydrogen ($CO:H_2=1$) were introduced into the autoclave. The system was heated to 140°–160° and allowed to react for 12 hours. The solution was then put into an evacuated Schlenck receiver flushed with nitrogen and then mixed with dried toluene (10:1 toluene:solution ratio). The solvent was decanted after 12 hours. The tar-like oily residue remaining was extracted with acetone. The resulting filtrate was divided in two equal aliquots. One of them is vacuum dried and the resulting solid has a Cs:Rh ratio and an infrared spectrum as expected for $Cs_2[Rh_9P(CO)_{21}]$. The second aliquot was treated with an equal volume of an isopropanol solution of $[C_6H_5CH_2N(C_2H_5)_3]Cl$. The precipitate formed was filtered away, washed with fresh isopropanol and vacuum dried. Crystals are grown by the slow diffusion method using an acetone-isopropanol solvent mixture. This material was used for analytical analysis.

Elemental analysis of $[C_6H_5CH_2N(C_2H_5)_3]_2[Rh_9P(CO)_{21}]CH_3C(O)CH_3$ is as follows:

|    | Percent Calculated | Percent Found (1) |       |
|----|--------------------|-------------------|-------|
| C  | 30.19              | 28.05,            | 28.03 |
| H  | 2.54               | 2.45,             | 2.58  |
| N  | 1.41               | 1.41              | 1.51  |
| P  | 1.56               | 1.37,             | 1.54  |
| Rh | 46.60              | 47.00,            | 47.14 |

(1) Samples were analyzed twice.

[18]-crown-6 ether 7.0 millimoles (mmol) of N-methylmorpholine, the indicated type and amount of salt, and 1.5 millimoles (mmol) of rhodium carbonyl phosphido cluster compound, wherein the anion cluster is of the following empirical formula:

$[Rh_9P_1(CO)_{21}]^{-2}$.

The reactor was sealed and charged with a gaseous mixture, containing equal molar amounts of carbon monoxide and hydrogen, to a pressure of 6,000 pounds per square inch (psig). Heat was applied to the reactor and its contents; when the temperature of the mixture inside the reactor reached 280° C., as measured by a suitably placed thermocouple, and additional adjustment of carbon monoxide and hydrogen ($H_2:CO=1:1$ mole ratio) was made to bring the pressure back to 15000 psig. The temperature (in °C) was maintained at the desired value for 3 hours. During this period of time additional carbon monoxide and hydrogen was added whenever the pressure inside the reactor dropped below about 14,500 psig. With these added repressurizations the pressure inside the reactor was maintained at 15,000 psig $\pm 500$ psig over the entire 3 hour period.

After the 3 hour period, the vessel and its contents were cooled to room temperature, the excess gas vented and the reaction product mixture was removed. Analysis of the reaction product mixture was made by gas chromatographic analysis using a Hewlett Packard FM TM model 810 Research Chromatograph.

Rhodium recovery was determined by atomic absorption analysis of the contents of the reactor after the venting of the unreacted gases at the end of the reaction. A further analysis was run on a "wash" of the reactor. The wash of the reactor consisted of charging to the reactor 100 cc of the solvent used for the experiment, and bringing the reactor and its contents to a temperature of 160° C. and a pressure of 14,000 to 15,000 psig and maintaining these conditions for a period of 30 minutes. The reactor was then cooled and the unreacted gases vented and an atomic absorption analysis for rhodium was rund on the reactor's contents. The rhodium recovery values recited below are the percent rhodium based on the total rhodium charged to the reactor that is soluble or suspended in the reaction mixture plus the wash after the specified time.

The temperature, cation in the cluster, salt, analysis of the product mixture, and rhodium recovery (percent of initial charge) are set forth in Table I.

TABLE I

| Example | T(° C.) | Cation in Cluster | Salt (mmoles) | Rate (Mole, Liter$^{-1}$; Hours$^{-1}$) | | Rh Recovered In Solution (%) |
|---------|---------|-------------------|----------------|---------------------------------|---|------------------------------|
|         |         |                   |                | $CH_3OH$ | $HOCH_2CH_2OH$ |                              |
| 2 | 260 | Cs | — | — | 0.13 | 95 |
| 3 | 270 | Cs | — | 0.08 | 0.02 | 113[1] |
| 4 | 270 | $[C_6H_5CH_2N(C_2H_5)_3]$ | — | — | 0.16 | 78 |
| 5 | 270 | Cs | Cesium benzoate(0.32) | 0.07 | 0.02 | 100 |
| 6 | 270 | Cs | Cesium benzoate(0.37) | 0.12 | 0.15 | 100 |
| 7 | 280 | Cs | — | 0.24 | 0.24 | 85 |

[1] indicates quantitative rhodium recovery.

EXAMPLES 2 TO 7

A 150 ml. capacity stainless steel reactor capable of withstanding pressure up to 7,000 atmospheres was charged with a premix of 75 cubic centimeters (cc) of

What is claimed is:

1. A rhodium carbonyl phosphido cluster compound which is the combination of an anion of the following empirical formula:

$[Rh_9P(CO)_{21}]^{-2}$ associated with a cation.

2. A rhodium carbonyl phosphido cluster compound of the following formula:

$Cs_2[Rh_9P(CO)_{21}]$.

3. A rhodium carbonyl phosphido cluster compound of the following formula:

$[C_6H_5CH_2N(C_2H_5)_3]_2[Rh_9P(CO)_{21}]CH_3C(O)CH_3$.

* * * * *

UNITED STATES PATENT AND TRADEMARK OFFICE
CERTIFICATE OF CORRECTION

PATENT NO. : 4,257,972           Page 1 of 3
DATED : March 24, 1981
INVENTOR(S) : José L. Vidal and Wellington E. Walker It is certified that error appears in the above—identified patent and that said Letters Patent is hereby corrected as shown below:

Col. 1, line 46, "U.s." should read --U.S.--.

Col. 2, line 55, "$[(C_6H_5)_3P]_2N^{30}$, etc." should read --$[(C_6H_5)_3P]_2N^+$, etc.--.

Col. 2, last line, "p-methylsulfo-" should read --$\underline{p}$-methylsulfo- --.

Col. 3, line 5, "para" should read --$\underline{para}$--.

Col. 3, line 27, "n-propyl" should read --$\underline{n}$-propyl--.

Col. 3, line 27, "n-butyl" should read --$\underline{n}$-butyl--.

Col. 3, line 32, "t-butylphenyl" should read --$\underline{t}$-putylphenyl--.

Col. 3, line 33, "beta-phenylethyl" should read --$\underline{beta}$-phenylethyl--.

Col. 3, line 34, "beta-hydrox-" should read --$\underline{beta}$-hydrox- --.

Col. 3, line 37, "n" should read --$\underline{n}$--.

Col. 3, line 38, "x" should read --$\underline{x}$--.

Col. 3, line 43, "Y" should read --$\underline{Y}$--.

Col. 3, line 54, "Y" should read --$\underline{Y}$--.

Col. 3, line 59, "311" should read --$\underline{311}$--.

UNITED STATES PATENT AND TRADEMARK OFFICE
CERTIFICATE OF CORRECTION

PATENT NO. : 4,257,972

DATED : March 24, 1981

INVENTOR(S) : José L. Vidal and Wellington E. Walker

It is certified that error appears in the above—identified patent and that said Letters Patent is hereby corrected as shown below:

Col. 4, line 65, "received" should read --receiver,--.

Col. 5, line 5, "cary" should read --vary--.

Col. 5, line 6, delete "and".

Col. 6, line 11, "di-n-propanolamine" should read --di-$\underline{n}$-propanolamine--.

Col. 6, line 44, "n-propyla-" should read --$\underline{n}$-propyla- --.

Col. 6, line 52, "tetra-n-" should read --tetra-$\underline{n}$- --.

Col. 6, line 53, "o-phenylenedia-" should read --$\underline{o}$-phenylenedia- --.

Col. 6, line 54, "m-phenylenediamine, p-phenylenediamine, p-" should read --$\underline{m}$-phenylenediamine, $\underline{p}$-phenylenediamine, $\underline{p}$- --.

Col. 6, line 58, "p-toluidine, o-3-" should read --$\underline{p}$-toluidine, $\underline{o}$-3- --.

Col. 6, line 59, "p-2-xylidine" should read --$\underline{p}$-2-xylidine--.

Col. 8, lines 47, 48, "in situ" should be underscored.

Col. 10, line 1, insert a comma (,) after "ether".

Col. 10, line 2, delete the period (.) after "salt".

Col. 10, line 30, "FM TM" should read --FM$\underline{^{TM}}$--.

UNITED STATES PATENT AND TRADEMARK OFFICE
CERTIFICATE OF CORRECTION

PATENT NO. : 4,257,972

DATED : March 24, 1981

INVENTOR(S) : José L. Vidal and Wellington E. Walker

It is certified that error appears in the above—identified patent and that said Letters Patent is hereby corrected as shown below:

Col. 10, line 42, "rund" should read --run--.

Signed and Sealed this

Tenth Day of November 1981

[SEAL]

Attest:

GERALD J. MOSSINGHOFF

Attesting Officer

Commissioner of Patents and Trademarks